(12) United States Patent
Höfgen et al.

(10) Patent No.: US 6,248,936 B1
(45) Date of Patent: Jun. 19, 2001

(54) SUGARBEET STORAGE-ROOT-TISSUE-SPECIFIC REGULON

(75) Inventors: Rainer Höfgen; Holger Hesse, both of Berlin (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 09/125,984

(22) PCT Filed: Dec. 30, 1996

(86) PCT No.: PCT/EP96/05858

§ 371 Date: Feb. 16, 1999

§ 102(e) Date: Feb. 16, 1999

(87) PCT Pub. No.: WO97/32027

PCT Pub. Date: Sep. 4, 1997

(30) Foreign Application Priority Data

Feb. 29, 1996 (DE) ................................. 196 07 697

(51) Int. Cl.⁷ ................... C12N 5/04; C12N 15/29; C12N 15/82; C12N 15/90; A01H 5/00
(52) U.S. Cl. .............. 800/287; 435/320.1; 435/410; 435/419; 435/468; 536/23.6; 536/24.1; 800/298
(58) Field of Search ................. 435/69.1, 320.1, 435/410, 419, 468; 536/23.6, 24.1; 800/278, 287, 295, 298

(56) References Cited

FOREIGN PATENT DOCUMENTS

| 41 24 537 | 2/1992 | (DE) | C12N/15/11 |
|---|---|---|---|
| WO94/28146 | 5/1994 | (WO) | C12N/15/82 |

OTHER PUBLICATIONS

Guarente et al, Trends in Genetics, vol. 8, pp. 27–32, 1992.*
Huang et al, Plant Physiol., vol. 104, pp. 293–294, 1994.*
Rowland, L.S., Yen–Ching, C., and Chourey, P.S., (1989), "Anaerobic Treatment Alters the Cell Specific Expression of Adh–1, Sh, and Sus Genes in Roots of Maize Seedlings", *Mol. Gen. Genet.*, 218:33–40.
Fieuw, S. and Willenbrink, J. (1990), "Sugar Transport and Sugar–Metabolizing Enzymes in Sugar Beet Storage Roots (*Beta vulgaris* ssp. *altissima*)", *J. Plant Physiol.*, 137:216–223.

Maraña, C., García–Olmedo, F., and Carbonero, P., (1990) "Differential Expression of Two Types of Sucrose Synthase–Encoding Genes in Wheat in Response to Anaerobiosis, Cold Shock and Light" *Gene.*, 88:167–172.
Yang, N.S., and Russell, D., (1990), "Maize Sucrose Synthase–1 Promoter Directs Phloem Cell–Specific Expression of Gus Gene in Transgenic Tobacco Plants", *Proc. Natl. Acad. Sci. USA*, 87:4144–4148.
Crespi, Martin D., Zabaleta, Eduardo J., Pontis, Horacio G., Salerno, Graciela L., (1991), "Sucrose Synthase Expression During Cold Acclimation in Wheat", *Plant Physiol.*, 96:887–891.
Martin, T., Frommer, W.B., Salanoubat, M., and Willmitzer, L., (1993), "Expression of an Arabidopsis Sucrose Synthase Gene Indicates a Role in Metabolization of Sucrose Both During Phloem Loading and in Sink Organs", *The Plant Journal*, 4(2):367–377.
Sturm, A., Šebková, V., Lorenz, K., Hardeggar, M., Lienhard, S., and Unger, C., (1995) "Development–and Organ–Specific Expression of the Genes for Sucropse Synthase and Three Isoenzymes of Acid β–fructofuranosidase in Carrot", *Planta.* 195:601–610.
Šebková, V., Unger C., Hardeggar M., and Sturm A., (1995) "Biochemical, Physiological, and Molecular Characterization of Sucrose Synthase from *Daucus carota*", *Plant Physiol.* 108:75–83.
Holger Hesse, Uwe Sonnewald and Lothar Willmitzer, (1995), Cloning and Expression Analysis of Sucrose–Phosphate Synthase from Sugar Beet (*Beta vulgaris* L.), *Mol. Gen. Genet.*, 247:515–520.
Holger Hesse and Lothar Willmitzer, (1996), "Expression Analysis of a Sucrose Synthase Gene from Sugar Beet (*Beta vulgaris* L.)", *Plant Molecular Biology*, 30:863–872.

* cited by examiner

*Primary Examiner*—Gary Benzion
*Assistant Examiner*—Ashwin Mehta
(74) *Attorney, Agent, or Firm*—Needle & Rosenberg, P.C.

(57) ABSTRACT

The present invention relates to a new regulon which in storage roots of the sugar beet (Beta vulgaris L.) constitutively expresses the gene which is under its control, such that a transition from anaerobic to aerobic conditions, a transition from normal temperature (appr. 22° C.) to cold temperature (appr. 4° C.) and changing sugar concentrations do not alter the transcription activity of the regulon in the storage root tissue.

12 Claims, 2 Drawing Sheets

SEQUENCE LISTING

```
<160> NUMBER OF SEQ ID NOS: 2

<210> SEQ ID NO: 1
<211> LENGTH: 210
<212> TYPE: DNA
<213> ORGANISM: Beta vulgaris
<220> FEATURE:
<221> NAME/KEY: CDS
<222> LOCATION: (34)...(210)

<400> SEQUENCE: 1
gcggccgctc cccaaagttc atcctcatca aaa atg gcg ccc aaa tta aca aga         54
                                    Met Ala Pro Lys Leu Thr Arg
                                     1               5 atc cct agt atg aga gag aga gtg gaa gac act ctc tct gtt cat cgt        102
Ile Pro Ser Met Arg Glu Arg Val Glu Asp Thr Leu Ser Val His Arg
         10                  15                  20 aac gag ctc gtc tct ctt ctc tcc aag tat gtt gct caa ggg aag tgt        150
Asn Glu Leu Val Ser Leu Leu Ser Lys Tyr Val Ala Gln Gly Lys Cys
     25                  30                  35 tta ttg caa cct cat cat ctg att gat gga tta gaa agt gta atc ggc        198
Leu Leu Gln Pro His His Leu Ile Asp Gly Leu Glu Ser Val Ile Gly
 40                  45                  50                  55 gaa gat aaa ggc                                                        210
Glu Asp Lys Gly <210> SEQ ID NO: 2
<211> LENGTH: 59
<212> TYPE: PRT
<213> ORGANISM: Beta vulgaris

<400> SEQUENCE: 2

Met Ala Pro Lys Leu Thr Arg Ile Pro Ser Met Arg Glu Arg Val Glu
 1               5                  10                  15
```

```
Asp Thr Leu Ser Val His Arg Asn Glu Leu Val Ser Leu Leu Ser Lys
            20                  25                  30

Tyr Val Ala Gln Gly Lys Cys Leu Leu Gln Pro His His Leu Ile Asp
            35                  40                  45

Gly Leu Glu Ser Val Ile Gly Glu Asp Lys Gly
            50                  55
```

SUGARBEET STORAGE-ROOT-TISSUE-SPECIFIC REGULON

The present invention relates to a new plant-based regulon that shows a storage root specific expression pattern.

Plants are often exposed to rapidly changing ambient conditions. This makes it advantageous for plants to be able to resist to quickly changing ambient influences. The adaption to new environment conditions is carried out via a change of expression in all kinds of genes. For example the Sh1-gene from maize is induced under anaerobic conditions. (Rowland et al., Mol. Gen. Genet. 218:33–40 (1989)). The situation for sucrose synthase genes from potato or rice is similar. (Salanoubat et al., Gene 84:181–185 (1989) and Wang et al. Plant Mol. Biol. 18:1191–1194 (1992)). A further environmental factor that contributes to an increased expression of sucrose synthase is a lower temperature. (Marana et al., Gene 88:167–172 (1990) and Crespi et al., Plant Physiol. 96:887–891 (1991)). Moreover, a limited supply of carbohydrates causes an increase in transcription of the maize gene Sh1, while under the same conditions the Susl gene is expressed with a reduced expression rate (Maas et al., EMBO J. 9:3447–3452 (1990) and Koch et al, Plant Cell 4:59–69 (1992)). Of wheat and arabidopsis it is moreover known that coldness treatment induces the sucrose synthase genes (Marana et al., Gene 88:167–172 (1990), Crespi et al., Plant Physiol. 96: 887–891 (1991) und Martin et al., Plant J. 4:367–377 (1993)). The maize gene Sh1, the potato's sucrose synthase gene and the wheat gene Ssl show an increased expression under anaerobic conditions (Rowland et al., Mol. Gen. Genet. 218:33–40 (1989), Salanoubat et al., Gene 84:181–185 (1989) and Marana et al., Gene 88:167–172 (1990)). Finally, the maize gene Sh1 is also influenced by an external supply of sucrose (Martin et al. Plant J. 4:367–377 (1993) and Koch et al., Plant Cell 4:59–69 (1992)).

The present invention addresses the technical problem of providing a new regulon which displays an expression pattern that is not yet known from any regulatory elements disclosed in the prior art and that can be advantageously used for the expression of genes under its control.

The invention solves this problem by a regulon which, within the sugar beet (Beta vulgaris L.)'s storage root tissue and independently of either the ambient oxygen concentration or the ambient temperature or the sugar concentration in the root cells, constitutively expresses the gene under its control.

Figure 1:
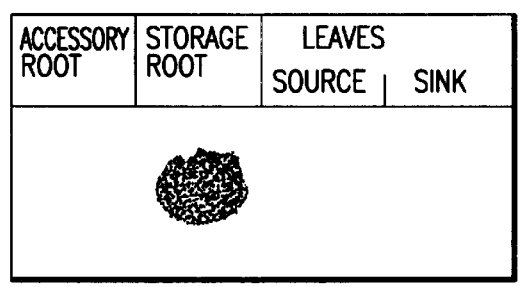
FIG. 1 shows the expression of the SBSSI gene in various tissues of the sugar beet B. vulgaris.

In the following, "regulon" denotes a DNA sequence which controls the expression of a gene under its control depending on endogeneous and exogeneous factors. Among such factors are for example inductors, repressors and similar DNA binding proteins as well as ambient influences, such as temperature changes or changes in concentration of ambient oxygen, and tissue injuries or the supply of nutritive substances. A regulon can comprise several elements, such as enhancers, silencers or promoters. But a regulon must comprise at least one regulatory element which is in charge of the transcription of the gene under its control.

By "constitutive" in the following it is meant that the transcription activity of the regulon under changing conditions, such as during transition from normal temperature appr. (22° C.) to coldness (appr. 4° C.) or during transition from aerobic to anaerobic conditions, changes by a factor of less than 3. Consequently, a regulon is considered "inducible" or "repressible", when its transcription activity changes under the inducing resp. erepressing conditions by a factor of more than 3.

The regulon of this invention has as a salient feature that in storage root tissue it leads to constitutive expression of the gene under its control. In its natural environment within the genome of Beta vulgaris L. it controls the expression of the sucrose synthase gene SBSSI (cf H. Hesse, dissertation, Berlin Free University chemistry department, 1993). It is worth noting that a change of oxygen concentration does not, as with anaerobiosis, affect the regulon's transcription activity. Nor does a change of ambient temperature, such as lowering the temperature from 22° C. to 4° C. (i.e. under cold shock), lead to a change of the gene's expression und the control of the regulon of the invention in storage roots. Finally, the regulon of the invention is also constitutively transcriptionally active under all kinds of sugar concentrations. For example, adding sucrose, glucose resp. mannose doesn't lead to a change of the expression of the gene controlled by the regulon of the invention.

The finding that the regulon of the invention in storage root tissue occurs in a permanently active state, independently of oxygen and/or temperature conditions as well as the sugar concentration, distinguishes the regulon of the invention from all so far known elements which participate in the expression of plant genes, especially sucrose synthase genes.

For example, all so far known promoters of sucrose synthase genes can be induced by anaerobiosis or cold; i.e. these known promoters are not constitutive promoters.

The regulon of the invention can for instance be isolated from a plant DNA bank, in which case for the purpose of isolation the DNA probe according to SEQ ID No.1 can be used. The hybridisation conditions suitable for searching the bank can easily be determined by the skilled person according to the relevant literature, such as described in Maniatis et al., Molecular Cloning, A Laboratory Manual, 1989, Cold Spring Harbor Laboratory Press.

Those clones that during searching of the genomic DNA bank were identified as positive with the probe can then be subjected to further investigations concerning their expression properties according to standard procedures. Thus, those sequences that hybridize with the probe can be isolated from the vectors that were used for producing the DNA bank and then be subjected to investigations in conventional expression cassettes concerning their transcription influencing properties.

In order to investigate the expression activity of the isolated fragments, one can introduce them into plasmids that are suitable for transformation of plant cells and that are stably integrated into the plant genome. For this the binary vectors BIN19 and pBI101, pBI101.2 and pBI101.3 could be used. The vector BIN19 has been described by Bevan (Nucl. Acids Res. 12 (1984), 8711–8721)) and is commercially available (Clontech Laboratories, Inc., USA). The derivates of the vector pBI101 were described by Jefferson et al. (Plant Mol. Biol. Rep. 5 (1987), 387–405) and are also commercially available (Clontech Laboratories, Inc., USA).

One can however use any plant transformation vectors, into which an expression cassette can be integrated and which enable the integration of the expression cassette into the plant genome.

The transformation method for plant cells, e.g. using Agrobacterium tumefaciens or Agro-bacterium rhizogenes, are known to the skilled person.

From the infected plant material (e.g. leaf parts, stalk segments, roots, but also protoplasts or suspension cultivated plant cells), the complete plants can then be regenerated in appropriate media which contain the desired antibiotics or biocides needed for selecting transformed cells.

The thus obtained plants are then investigated with respect to the presence of the introduced DNA. Usually the DNA that is introduced into plants moreover contains a selection marker which makes the transformed cells resistant against a biocide or an antibiotic such as kanamycine, G 418, bleomycine, hygromycine or phosphinotricine. From the transformed cells transgenic plants are then obtained in conventional manner (cf McCormick et al., Plant Cell Reports 5 (1986), 81–84)). The obtained transgenic plants can when necessary be further crossed with plants of a different genotype.

Finally the various plant tissues can be investigated as to whether the introduced DNA fragment exhibits the expression pattern of the regulon of the invention. In this case as indicator for the expression activity of the introduced fragment an arbitrary reporter gene can be used, as long as it is under the transcription control of the fragment to be tested.

DNA sequences which are placed within the expression cassette subsequent to the fragment to be tested, can represent arbitrary coding sequences that lead to a detectable final product.

The testing fragment need not be tested within a sugar beet plant, but preferably potato is used as a host plant for the testing fragment. The transformation of potato plants with binary plasmids is described among others in Deblaere et al., Nucl. Acids Res. (1985), 4777–4788. The use of potato plants for testing the fragments with respect to their expression pattern is based on the finding, that a regulon that shows a certain expression pattern in storage root cells of the sugar beet tends to show the same pattern in the bulbs of potato plants. This means, that the regulon of the invention is also continuously transcriptionally active to the same degree in cells of the potato bulb, regardless of the ambient oxygen concentration, the ambient temperature and the sugar concentration in the cells of the potato bulb.

The regulon of the invention in B. vulgaris controls the expression of the sucrose synthase gene (SBSSI).

Preferably the regulon of the invention is the regulatory element from the 5 kb long region adjacent to the 5' end of the transcription start of the SBSSI gene in the genome of B. vulgaris. The transcription start of the protein coding sequence is indicated in SEQ ID No. 2.

As regulons of the invention, not only naturally occurring regulons such as those obtainable by probe SEQ ID No. 1, are conceivable, but also derivates based thereupon (e.g. regulon(s) carrying insertion(s), deletion(s) and/or substitution(s)), as long as these derivates show at least 20% of the transcription activity of the sugar beet's SBSS1 gene's regulon under comparable conditions. Preferably these derivates will show 100% or more of the activity of the sugar beet regulon.

The regulon of the invention can e.g. be advantageously employed for producing a recombinant DNA, in which a gene of interest is under the control of the regulon. Such a recombinant DNA thus allows the expression of the gene product under conditions, under which so far no high expression rates had been obtained. E.g. the regulon of the invention is also transcription active under high sugar concentrations in the ambient medium.

By introducing a recombinant DNA containing the regulon of the invention into a plant cell, the plant cell can be endowed with new properties, in such a way that the regulon of the invention makes possible the expression of products in the cell, which the plant cell could otherwise not express or only express with different expression rates.

Thus, the regulon of the invention allows the production of new plants with improved qualities such as homogeneous expression of arbitrary genes under the control of the regulon of the invention regardless of ambient influences such as oxygen deficiency, temperature fluctuations and/or sugar supply.

A transgenic plant can be produced by introduction of the regulon of the invention into the plant cell in a manner known per se and regeneration of the plant therefrom. The following examples serve to explain the invention.

EXAMPLES

Cloning Method

For cloning in E. coli, the vectors pBluescript SK (stratagene) and lambdaEMBL 3 (Frischauf et al. (1983), J. Mol. Biol. 170, 827–842) were used. For the purpose of plant transformation, the DNA fragments were cloned into the binary vectors BIN 19 (Bevan (1984), Nucl. Acids Res. 12, 8711–8720) and pBI101 derivatives (Jefferson et al., (1987) Plant Mol. Biol. Rep. 5, 387–405).

Bacterial Strains

XL-1 Blue (Stratagene) E. coli strain was used for the plasmid vectors named above and strain LE2392 (Stratagene) was used for the phage vectors. The transformation of binary plasmids in the potato plants was carried out by means of Agrobacterium tumefaciens strain C58C1 pGV2260 (Deblaere et al., Nucl. Acids Res. (1985), 4777–4788).

Transformation of Agrobacterium Tumefaciens

The transfer of DNA into the bacteria was achieved by direct transformation according to the method of Höfgen & Willmitzer (Nucl. Acids Res. 16 (1988), 9877). The transformed DNA was then successfully isolated and after an appropriate restriction cleavage it was analysed by gel electrophoresis.

Transformation of Potato 10 small leaves of a sterile potato culture scraped with a scalpel (Solanum tuberosum L. cv. Desiree) were placed in 10 ml MS-Medium (Murashige & Skoog, Physiol. Plant. 15 (1962), 473–497) containing 2% sucrose, in such a way that the medium contained 50 µl of an Agrobacterium tumefaciens overnight culture grown selectively. After 3–5 minutes of light shaking further incubation followed for 2 days in the dark. Thereafter the leaves were placed for callus induction on MS-Medium with 1.6% glucose, 5 mg/l naphthyl acetic acid, 0.2 mg/l benzyl amino purine, 250 mg/l claforane, 50 mg/l kanamycine resp. 1 mg/l hygromycin B and 0.8% bacto agar. After a one-week incubation at 25° C. and 3000 lux, the leaves were placed for sprout expression on MS-Medium with 1.6% glucose, 1.4 mg/l Zeatin ribose, 20 mg/l naphthyl acetic acid, 20 mg/l Giberellic acid, 250 mg/l claforane, 50 mg/l kanamycine resp. 3 mg/l hygromycin and 0.8% bacto agar.

Radioactive Labelling of DNA Fragments.

The radioactive labelling of DNA fragments was performed using a DNA-Random Primer Labelling Kit of Boehringer (Germany.) according to the manufacturer's instructions.

Plant Cultivation

The potato plants were cultivated in a greenhouse under the following conditions:

Period of light 16 hrs at 25000 Lux and 22° C.
Period of darkness 8 hrs at 15C.
Air humidity 60%.

Analysis of Genomic DNA from Transgenic Potato Plants

The isolation of genomic plant DNA was carried out according to Rogers & Bendich (1985; Plant Mol. Biol. 5, 69–76). The characterisation of the DNA from the transgenic potato plants was done by restriction mapping and Southern Blot analyses.

Beta-Glucuronidase Activity Test. (GUS-Assay)

The beta-glucuronidase is a bacterial enzyme that hydrolyzes beta-glucuronide and makes possible both a quantitative and a histochemical determination of activity. The determination of activity was performed according to Jefferson et al. (EMBO J. 6, (1987) 3901–3907). The tissue probes were incubated in 1 mM XGluc, 50 mM Sodium phosphate, pH 7.0 and 0.1% Tween 20 until the desired blue coloring developed. This test allows the determination of the expression pattern of any sequence in the different tissues of a transgenic plant. The transcription regulating characteristics of a DNA segment of approximately 4 kb length, which extended starting from the start codon of the SBSSI gene, was cloned in various binary vectors, such as pBIN19 and pBI101-derivatives. The vectors contain the coding region of the beta-glucuronidase gene from $Escherichia\ coli$ as the reporter gene. This reporter gene indicates, under the control of fragment introduced, in which tissues transcription of the reporter gene occurs under the prevailing selected environmental effects.

The fusion products from regulon and GUS were introduced into the potato plants via a gene transfer by means of the Agrobacteriae. The leaf, stem, bulb, and roots were investigated concerning the activity of beta-glucuronidase in transformants, obtained independently of each other, in which the presence of intact, not rearranged chimeric fusion product was demonstrated by means of Southern Blot analyses.

The isolation of clones containing DNA fragments, which show the transcription regulating characteristics of the regulon of the SBSS1 gene of $Beta\ vulgaris$ L.

The 5' region of a DNA sequence, which codes for the sucrose synthase gene from $B.\ vulgaris$, served as a probe to isolate clones from a genomic DNA bank of $B.$ vulgaris breeding line 5S 0026 (Kleinwanzlebener Saatzucht AG). The DNA probe used possesses the sequence SEQ ID No. 1.

Subsequently a genomic DNA bank was established. DNA was isolated from the leaves of 3- to 4-month-old sugar beet plants of the 5S 0026 breeding line essentially according to the method of Dellaporta et al (Plant Mol. Biol. Rep. 1 (1983), 19–21). The genomic DNA was partially digested with 10 different concentrations of the Sau3A enzyme at 37° C. for 15 minutes. Finally heat inactivation of the restriction enzyme took place for 30 minutes at 70° C. The aliquots of the different restriction incubations were separated on a 0.7% agarose gel. Fractions with cut, but still highly molecular DNA were pooled and for 30 minutes treated with alkaline phosphatase. Finally the DNA was cleaned by phenolic extraction and by the addition of 1/10 volume of sodium acetate and 2 volumes of 96% ethanol precipitated. The DNA was centrifuged and the pellet was washed with 70% ethanol. The DNA was dried briefly and dissolved in water. Lambda EMBL 3 arms precut with BamHI were used for the cloning of the DNA prepared in this way. (Stratagene GmbH, Heidelberg, Germany). The packing into the phage heads took place with the use of the Gigapack II Gold Kit (Stratagene GmbH, Heidelberg, Germany) according to the instructions of the manufacturer.

Approximately 200,000 plaques of this genomic DNA library were inspected for the desired sequences, in which case stringent conditions were employed (Hybridisation buffer with 50% formamide for 14 hours at 42° C. according to Sharrock et al., 1988, Mol. Gen. Genet. 213, 9–14.; Washing of the hybridisation filter after hybridisation in 2×SSC/0.1% SDS for 20 minutes and 0.1×SSC/0.1% SDS for 15 minutes always at 65° C.). Three clones from the phage clones hybridising with the probe were deposited in the DSM (Deutsche Sammlung für Mikroorganismen und Zelikulturen GmbH (Braunschweig)) provided with the designation SBSSI-lambda271, SBSSI-lambda321 and SBSSI-lambda351 after their cleaning.

Analysis of the Transcription Regulating Characteristics of the Regulon of the SBSSI Gene of $Beta\ Vulgaris$ L.

Diploid sugar beets of the KWS (Kleinwanzlebener Saatzucht AG, Einbeck, Germany) were used. The plants were cultivated in soil in the greenhouse under an alternating light/dark rhythm of 12.5 hours light (20° C.) and 11.5 hours darkness (13° C.).

In order to investigate the effect of cold and anaerobic treatment, the 3-month-old sugar beet plants were either exposed to light (12.5 hours) at 4° C. for 48 hours (treatment with cold) or immersed in water (anaerobic treatment) for 24 hours under normal greenhouse conditions. The control plants were kept under greenhouse conditions for the same duration. Each experiment was carried out three times.

The total RNA was isolated for the expression investigations according to the method of Logemann et al., Anal. Biochem. 163:21–26 (1987) from 3- to 4-month-old $Beta\ vulgaris$ plants, which had been cultivated in greenhouse. The RNA was fractionated on a 1.2% agarose/formaldehyde gel and transferred to a nylon membrane (Hybond N, Amersham). The hybridisation was carried out in 50% formamide-hybridisation buffer according to Sharrock et al., Mol. Gen. Genet. 213:9–14 (1988). The washing was carried out in 0.2×SSC/0.1% SDS at 65° C.

For the investigation of the effect of the sugar concentration on the expression, storage roots of the 3- to 4-month-old sugar beet plants were harvested. In each experiment 20 slices of 1.5 mm thickness and a surface of 1 cm$^2$ were randomly selected and incubated together in the incubation medium. The incubation was performed in darkness at 25° C. The experiment was always carried out three times.

The expression of the sucrose synthase gene under the control of the regulon of the invention followed, in which the SEQ ID No. 1 probe was employed in the RNA-Blot experiments in order to determine the pattern of the m-RNA expression of the sucrose synthase in the different tissues, such as leaves, storage roots, and roots of $B.\ vulgaris$. The regulon of the invention results in a strong expression of the SBSSI gene in the storage roots, whereas only an extremely small amount of expression was observed in the other tissues. In this analysis the total RNA of $Beta\ vulgaris$ was analysed using the SEQ ID No 1. probe. The result is shown in FIG. 1. In the Figure indicated 50 μg of the total RNA from "Sink"-leaves and "Source"-leaves, storage roots, or accessory roots was separated by means of gel electrophoresis on formaldehyde gel, transferred to a nylon membrane, and hybridised using the SEQ ID No. 1 probe. "Sink"-leaves are defined as small leaves, which are not yet independent in their energy metabolism and have to rely on energy supply from other plant components; "Source"-leaves are grown-up leaves with their own adequate energy suppply.

The Effect of a Cold Shock on the Transcription Activity of the Regulon of the Invention.

Figure 2:
FIG. 2 shows the influence of a coldness treatment on the expression of the SBSSI gene.

In order to investigate the effect of cold shock on the transcription activity of the regulon of the invention, the expression of the SBSS1 gene was studied during treatment with cold. For this purpose RNA was produced from the "Sink"-leaves and "Source"-leaves, storage roots, and accessory roots of plants, which were kept for 48 hours at 4° C. The analysis of RNA-blots through hybridisation with the SEQ ID No. 1 probe demonstrated that the treatment with cold exerted no effect on the expression pattern. The result is shown in FIG. 2. The total RNA of the sugar roots (50 pg) was separated on a formaldehyde gel, which was transferred to a nylon membrane, and hybridised using the SEQ ID No. 1 probe. The tracks 1 to 4 indicate RNA from the "Sink"-leaves and "Source"-leaves, storage roots, and accessory roots of plants 48 hours after the treatment with cold; the tracks 5 to 8 show the RNA from the control plants, which were cultivated in the greenhouse.

The Effect of Anaerobic Conditions on the Transcription Activity of the Regulon of the Invention.

Figure 3:
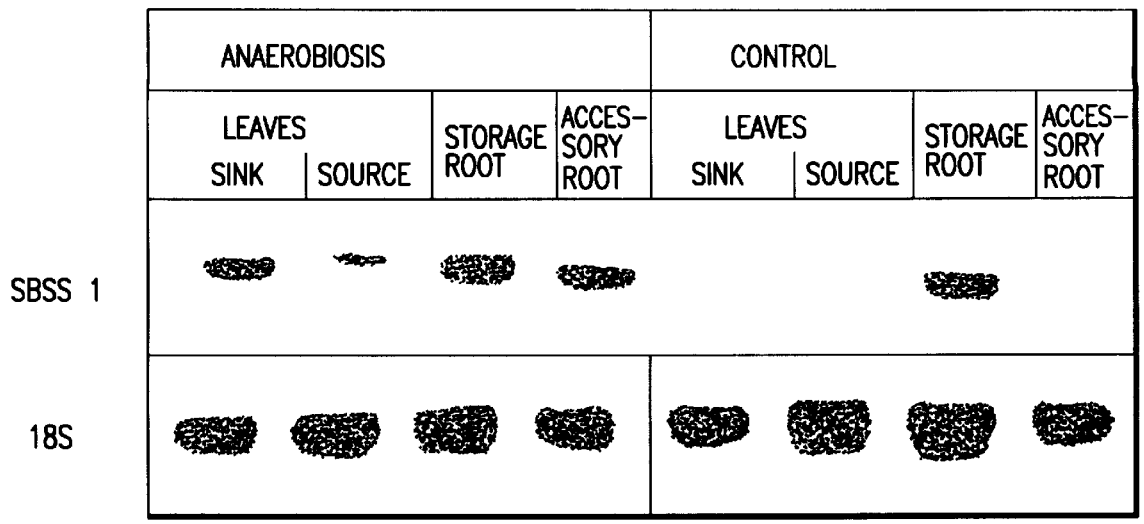
FIG. 3 shows the influence of anaerobiosis on the expression of the SBSSI gene.

The effect of anaerobiosis was investigated by immersing sugar beet plants in water for 24 hours. The level of the transcript rises under these anaerobic conditions in the "Sink"-leaves and "Source"-leaves, as well as in the accessory roots, while the transcription stays unchanged in the storage roots. The result is shown in FIG. 3. 50 pg of the total RNA was separated on a formaldehyde gel, transferred to a nylon membrane, and hybridised using the SEQ ID No. 1 probe. The tracks 1 to 4 indicate RNA 24 hours later under anaerobic conditions from the "Sink"-leaves and "Source"-leaves, storage roots, and accessory roots of plants; the tracks 5 to 8 show RNA from the control plants.

Figure 4:
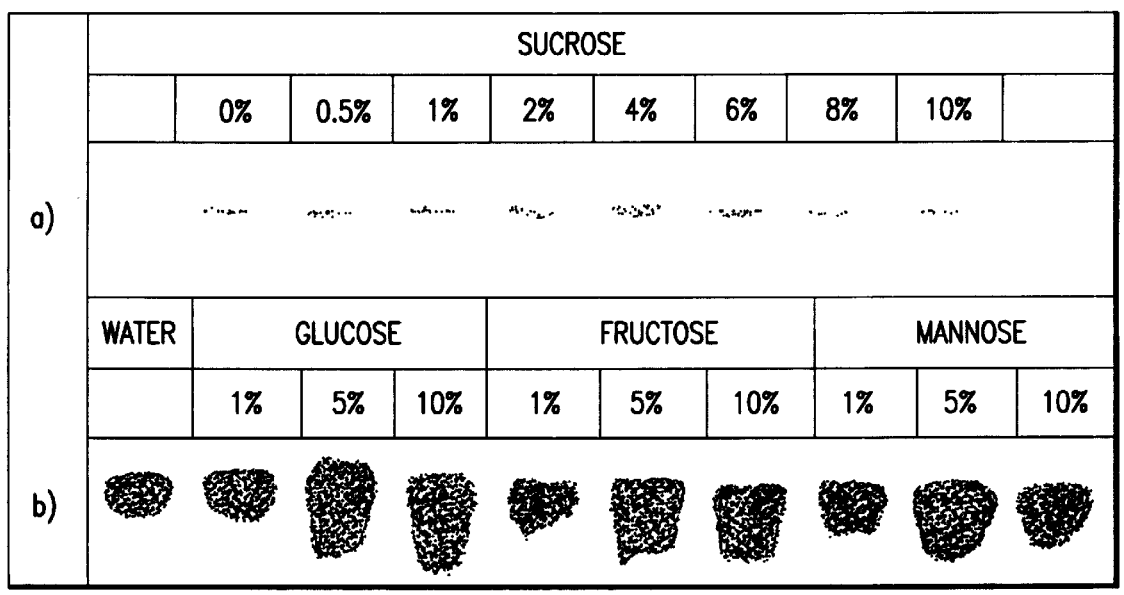
FIG. 4 shows the influence of various sugar concentrations on the expression of the SBSSI gene.

The Effect of a Sugar on the Transcription Activity of the Regulon of the Invention Storage root slices of plants, which were cultivated under greenhouse conditions, were exposed to different sucrose concentrations for 24 hours in the dark at room temperature:0, 0.5, 1, 1.5, 2, 4, 6, 8 and 10% (weight/volume) sucrose. Furthermore, tests were conducted with various sugars, such as glucose, fructose, and mannose at the concentrations of 1, 5 and 10% (weight/volume). FIG. 4. shows hybridisation of the same amounts of total RNA from different storage root samples. The transcripts were found at all sucrose, glucose, fructose, and mannose concentrations. No increase occurred in the transcription rate of sucrose synthase under these conditions. FIG. 4. shows the results of the RNA blots, in which equal amounts (50 μg) of the total RNA were employed, which were obtained from the storage roots after a 24-hour incubation period in the respective solutions. Blot (b) was exposed for 24 hours, whereas Blot (a) was exposed only for 4 hours.

The above results show that the regulon of the invention leads to a constitutive expression in the sugar beet storage roots in such a way that the transcription activity of the regulon is not altered neither under the influence of cold, nor under anaerobic conditions, nor under changing sugar conditions.

What is claimed is:

1. An isolated regulon comprising a DNA sequence selected from genomic plant DNA located within the 5 kb region adjacent to the 5' end of the transcription start of a genomic nucleic acid which hybridizes to SEQ ID NO:1 in hybridization buffer with 50% formamide for 14 hours at 42° C., followed by washing in 2×SSC/0.1% SDS for 20 minutes and 0.1×SSC/0.1% SDS for 15 minutes at 65° C., and wherein said isolated regulon constitutively expresses a gene under its control, regardless of ambient oxygen concentration, ambient temperature, or root cells' sugar concentration, and has the transcription regulatory activity of the *Beta vulgaris* SBSSI gene regulon, and wherein the isolated regulon is active in storage root tissue of sugar beet.

2. An isolated regulon according to claim 1, wherein the regulon in its natural environment in the genome of the sugar beet controls the expression of the sucrose synthase gene.

3. An isolated regulon of claim 1, wherein the genomic plant DNA is from sugar beet.

4. An isolated regulon of claim 3, wherein the DNA sequence occurs within 5 kb of the 5' end of the transcriptional start nucleotide of the sucrose synthase gene.

5. A process for preparing a transgenic plant comprising the steps of introducing the regulon of claim 1, 2, 3 or 4 into a plant cell and regenerating a transgenic plant from the plant cell.

6. A recombinant DNA, comprising the regulon of claims 1, 2, 3, or 4 and a gene to be expressed under control of the regulon.

7. The recombinant DNA of claim 6, wherein the gene is heterologous with respect to the regulon.

8. A plant transformation vector, comprising the recombinant DNA of claim 6.

9. A method for expressing a polypeptide constitutively in plant storage root tissue comprising transforming a plant cell with the plant transformation vector of claim 8 and regenerating plants from the transformed plant cell.

10. A plant cell, comprising the recombinant DNA of claim 6.

11. A transgenic plant, comprising the recombinant DNA of claim 6.

12. An isolated nucleic acid which hybridizes to SEQ ID NO:1 in hybridization buffer with 50% formamide for 14 hours at 42° C., followed by washing in 2×SSC/0.1% SDS for 20 minutes and 0.1×SSC/0.1% SDS for 15 minutes at 65° C., and wherein said isolated nucleic acid encodes the functional activity encoded by SEO ID NO:1.

* * * * *